(12) United States Patent
Geng et al.

(10) Patent No.: US 10,908,091 B2
(45) Date of Patent: Feb. 2, 2021

(54) BIOSENSOR, MANUFACTURING METHOD THEREOF AND BIOSENSING METHOD

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Yue Geng, Beijing (CN); Peizhi Cai, Beijing (CN); Fengchun Pang, Beijing (CN); Le Gu, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 82 days.

(21) Appl. No.: 16/323,007

(22) PCT Filed: May 11, 2018

(86) PCT No.: PCT/CN2018/086570
§ 371 (c)(1),
(2) Date: Feb. 4, 2019

(87) PCT Pub. No.: WO2018/223810
PCT Pub. Date: Dec. 13, 2018

(65) Prior Publication Data
US 2019/0187057 A1    Jun. 20, 2019

(30) Foreign Application Priority Data
Jun. 5, 2017   (CN) .......................... 2017 1 0415425

(51) Int. Cl.
*G01N 21/64*     (2006.01)
*G01N 33/543*    (2006.01)
(Continued)

(52) U.S. Cl.
CPC ..... *G01N 21/6486* (2013.01); *G01N 21/6428* (2013.01); *G01N 21/77* (2013.01);
(Continued)

(58) Field of Classification Search
CPC ........... G01N 21/6486; G01N 21/6428; G01N 2021/6439; G01N 21/77;
(Continued)

(56) References Cited

U.S. PATENT DOCUMENTS 6,096,559 A * 8/2000 Thundat ............... G01N 29/036
422/51
7,560,070 B1 * 7/2009 Baller ............... G01N 33/54373
422/50
(Continued)

FOREIGN PATENT DOCUMENTS

CN     1372135 A     10/2002
CN     102413761 A    4/2012
(Continued)

OTHER PUBLICATIONS

Chinese Office Action in corresponding Chinese Application No. 201710415425.2 dated Feb. 2, 2019 (an English translation attached hereto). 24 pages.
(Continued)

*Primary Examiner* — John R Lee
(74) *Attorney, Agent, or Firm* — Leason Ellis LLP

(57) ABSTRACT

A biosensor, and a preparation and biosensing method therefor. The biosensor includes: a sensing substrate, wherein a plurality of sensing suspending arms arranged in an array are arranged on the sensing substrate, and the sensing suspending arms have identification markers; and a detection substrate, the detection substrate including a plurality of light detection assemblies arranged in an array, wherein the light detection assemblies and the sensing
(Continued)

suspending arms are arranged in one-to-one correspondence, each of the light detection assemblies includes a photodiode and a thin film transistor, and the photodiode is connected to the thin film transistor.

16 Claims, 5 Drawing Sheets

(51) Int. Cl.
G01N 21/77 (2006.01)
G01N 21/01 (2006.01)
A61B 5/00 (2006.01)
(52) U.S. Cl.
CPC ...... *G01N 33/54366* (2013.01); *A61B 5/0071* (2013.01); *G01N 2021/0106* (2013.01); *G01N 2021/7756* (2013.01); *G01N 2021/7783* (2013.01); *G01N 2021/7793* (2013.01); *G01N 2021/7796* (2013.01)
(58) Field of Classification Search
CPC ... G01N 2021/7756; G01N 2021/7769; G01N 2021/7783; G01N 2021/7786; G01N 2021/7793; G01N 2021/7796; G01N 2021/0106; G01N 33/54366; G01N 33/54386; A61B 5/0071
See application file for complete search history.

(56) References Cited

U.S. PATENT DOCUMENTS

| | | | | |
|---|---|---|---|---|
| 7,785,864 | B2* | 8/2010 | Kang | G01N 29/036 250/306 |
| 2002/0137084 | A1* | 9/2002 | Quate | C12Q 1/6816 435/6.12 |
| 2003/0027351 | A1* | 2/2003 | Manalis | G01N 21/41 436/165 |
| 2003/0073071 | A1* | 4/2003 | Fritz | G01N 33/5438 435/4 |
| 2004/0038426 | A1* | 2/2004 | Manalis | G01N 33/54366 436/514 |
| 2005/0221361 | A1* | 10/2005 | Norman | G01N 33/54366 435/6.16 |
| 2007/0172940 | A9* | 7/2007 | Manalis | B81C 1/00071 435/287.2 |
| 2007/0285843 | A1* | 12/2007 | Tran | G11C 13/0011 360/245.9 |
| 2012/0071734 | A1 | 3/2012 | Shimuta et al. | |
| 2012/0129269 | A1* | 5/2012 | Choi | G01J 3/02 436/164 |
| 2014/0256057 | A1 | 9/2014 | Ozawa et al. | |
| 2014/0295577 | A1 | 10/2014 | Matsuzawa et al. | |
| 2015/0173675 | A1 | 6/2015 | Shimizu | |
| 2015/0253313 | A1* | 9/2015 | Hwang | G01N 33/5302 422/82.01 |
| 2015/0369661 | A1* | 12/2015 | Lin | G06K 9/0004 250/227.11 |
| 2016/0242685 | A1 | 8/2016 | DeHennis et al. | |
| 2017/0059563 | A1* | 3/2017 | Smith | G01N 21/6454 |
| 2018/0052106 | A1* | 2/2018 | Gunning | C12Q 2563/107 |
| 2018/0172681 | A1* | 6/2018 | Katchman | G01N 33/6857 |
| 2019/0187057 | A1* | 6/2019 | Geng | G01N 21/6486 |

FOREIGN PATENT DOCUMENTS

| | | |
|---|---|---|
| CN | 103589627 A | 2/2014 |
| CN | 103857997 A | 6/2014 |
| CN | 103874916 A | 6/2014 |
| CN | 104739372 A | 7/2015 |
| CN | 205333638 U | 6/2016 |

OTHER PUBLICATIONS

International Search Report and Written Opinion in corresponding International Patent Application No. PCT/CN2018/086570 dated Aug. 20, 2018 (translation attached). 17 pages.

* cited by examiner

US 10,908,091 B2

BIOSENSOR, MANUFACTURING METHOD THEREOF AND BIOSENSING METHOD

CROSS-REFERENCE TO RELATED PATENT APPLICATIONS

This application is a U.S. National Stage Application under 35 U.S.C. § 371 of International Patent Application No. PCT/CN2018/086570, filed May 11, 2018, which claims the benefit of priority under 35 U.S.C. Section 119(e) of Chinese Patent Application number 201710415425.2 filed Jun. 5, 2017, both of which are incorporated by reference in their entireties. The International Application was published on Dec. 13, 2018, as International Publication No. WO 2018/223810 A1.

TECHNICAL FIELD

Embodiments of the present disclosure relate to a biosensor, a manufacturing method thereof and a biosensing method.

BACKGROUND

A biosensor is a device that uses biological material (including enzyme, antibody, nucleic acid, cells, tissue, etc.) in combination with a physicochemical method to detect a test object. Biosensors have the advantages of high sensitivity, high specificity, real-time detection and the like, and have wide application value in clinical examination, environmental monitoring, life science research and other fields. At present, the detection of biomolecules in biosensors, e.g., gene sequencing and protein detection, is generally based on fluorescent labeling detection with intuitive detection results and high detection accuracy. With the development of bio-detection technology, the demand for detection technology and corresponding biosensors (detection chips) has also increased. The development of microelectromechanical system (MEMS) technology has made it possible to implement various kinds of micron-sized high-precision sensors.

However, the current biosensor, manufacturing method thereof and biosensing method still have much room for improvement.

SUMMARY

At least one embodiment of the present disclosure provides a biosensor, a manufacturing method thereof and a biosensing method.

At one aspect of the present disclosure, an embodiment of the present disclosure provides a biosensor, comprising: a sensing substrate, a plurality of sensing cantilevers arranged in an array being disposed on the sensing substrate, and a recognition marker being disposed on the sensing cantilever; and a detection substrate, including a plurality of optical detection components arranged in an array, wherein the plurality of optical detection components are in one-to-one correspondence with the plurality of sensing cantilevers, the optical detection component includes a photodiode and a thin-film transistor, and the photodiode is connected with the thin-film transistor.

For example, the sensing cantilever is configured to be irradiated by visible light; and a projection of the sensing cantilever on the detection substrate coincides with at least one portion of the photodiode along an incident direction of the visible light.

For example, the recognition marker has a capability of performing a specific reaction with a determinand in a sample, and the sensing cantilever is configured to be bent towards the detection substrate after the determinand reacts with the recognition marker.

For example, the biosensor further comprises: a housing, defining a sensing space, at least one portion of the housing being configured to allow the visible light to be incident into the housing, wherein the sensing substrate and the detection substrate are arranged in the housing, and the detection substrate is disposed on a side of the sensing substrate away from the incident direction of the visible light.

For example, the photodiode is made from amorphous silicon.

For example, the photodiode is connected with a drain electrode of the thin-film transistor, and the detection substrate further includes: a plurality of gate lines, connected with gate electrodes of a plurality of thin-film transistors disposed in a same row or a same column; a plurality of source lines, connected with source electrodes of a plurality of thin-film transistors disposed in a same row or a same column; and a common electrode, connected with a pole of the photodiode not connected with the thin-film transistor.

For example, the biosensor further comprises at least one of the following: a light source, configured to irradiate the visible light to an inside of the housing; and a data analysis unit, connected with the plurality of source lines.

For example, the detection substrate further includes a base, the plurality of optical detection components are arranged in an array on the base; and the optical detection component includes: a gate electrode, disposed on the base; an active layer, disposed on a side of the gate electrode away from the base; a source electrode and a drain electrode, insulated from each other and disposed on a side of the active layer away from the gate electrode; a photodiode, disposed on a side of the drain electrode away from the active layer and connected with the drain electrode; and a common electrode, disposed on a side of the photodiode away from the drain electrode and connected with the photodiode. The arrangement position of each part in the above optical detection component is consistent with structures of the array substrate.

At another aspect, an embodiment of the present disclosure provides a method for manufacturing a biosensor, comprising: providing a sensing substrate, wherein a plurality of sensing cantilevers arranged in an array are disposed on the sensing substrate and a recognition marker is disposed on the sensing cantilever, and providing a detection substrate, wherein the detection substrate includes a plurality of optical detection components arranged in an array, the plurality of optical detection components are in one-to-one correspondence with the plurality of sensing cantilevers, the optical detection component includes a photodiode and a thin-film transistor, and the photodiode is connected with the thin-film transistor, and wherein the detection substrate is manufactured based on an array substrate of a display panel.

For example, the sensing cantilever is configured to be irradiated by visible light; and a projection of the sensing cantilever on the detection substrate coincides with at least one portion of the photodiode along an incident direction of the visible light.

For example, the recognition marker has a capability of performing a specific reaction with a determinand in a sample, and the sensing cantilever is configured to be bent towards the detection substrate after the determinand reacts with the recognition marker.

For example, the method for manufacturing the biosensor further comprises: providing a housing; and arranging the sensing substrate and the detection substrate in the housing, in which the detection substrate is disposed on a side of the sensing substrate away from an incident direction of the visible light.

For example, the method further comprises at least one of a following steps: arranging a light source, in which the light source is configured to irradiate visible light to an inside of the housing; and arranging a data analysis unit, in which the data analysis unit is connected with a thin-film transistor in the detection substrate.

At still another aspect, an embodiment of the present disclosure provides a biosensing method by utilizing the biosensor as mentioned above, comprising: supplying a sample to the housing; allowing the sensing cantilever to be bent under a condition that a determinand in the sample reacts with the recognition marker on the sensing cantilever; and monitoring an electrical signal of the detection substrate before and after bending of the sensing cantilever, determining whether there is determinand in the sample, so as to realize biosensing.

For example, the determining whether there is determinand in the sample is performed by comparing change of a source current of the thin-film transistor in the optical detection component on the detection substrate before and after supplying the sample to the housing.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

REFERENCE NUMERALS OF THE ACCOMPANYING DRAWINGS

Figure 1:
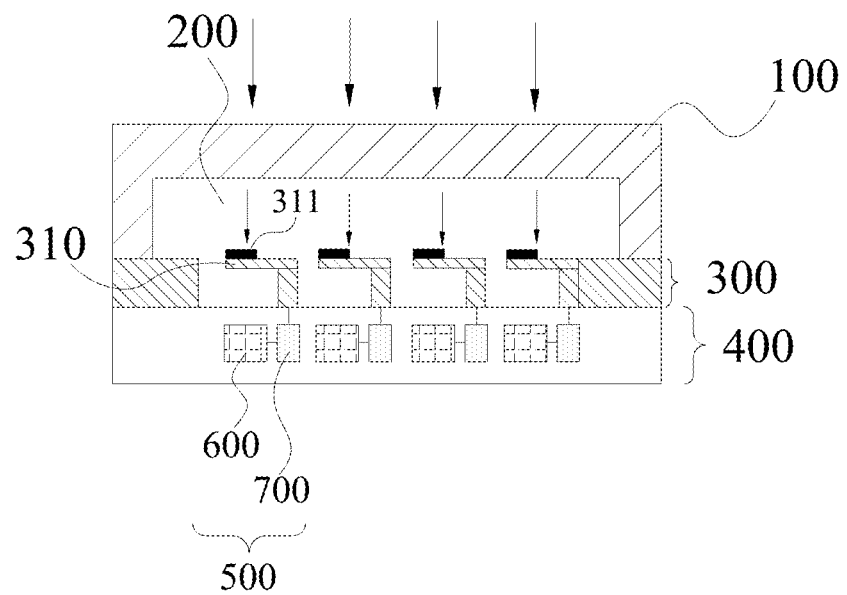
FIG. 1 is a schematic structural view of a biosensor provided by an embodiment of the present disclosure.

100: housing; 110: cover plate; 120: flow channel wall; 200: sensing space; 300: sensing substrate; 310: sensing cantilever, 311: recognition marker; 320: sensing cantilever projection; 400: detection substrate; 410: base; 500: optical detection component; 510: common electrode; 600: photodiode; 700: thin-film transistor; 710: gate electrode; 720: active layer, 730: source electrode; 740: drain electrode; 751: first insulating layer, 752: second insulating layer, 753: third insulating layer, 754: planarization layer; 755: pixel electrode; 800: light source; 900: data analysis unit.

DETAILED DESCRIPTION

Embodiments of the present disclosure will be in detail described hereinafter, and examples of the embodiments are shown in the drawings, in which the same or similar reference number is denoted as the same or similar members or the members with the same or similar function throughout. The described embodiments in conjunction with the accompanying drawings of the present disclosure are exemplary, only is used to explain the present disclosure and do not intend to limit the present disclosure.

In the description, the description with referring to the terms "an embodiment", "some embodiments", "example", "specific example" or "some examples" means that the specific feature, structure, material or character described with connection with the embodiment or example is included in at least one embodiment or example of the present disclosure. In the description, the schematic description of the above terms is not necessary to direct to the same embodiment or example. The described feature, structure, material or character may be combined in any suitable manner in any or a plurality of embodiments or examples. Further, in case of no conflict, different embodiments or examples and features in different embodiments or example described in the specification can be combined.

Further, the terms, such as "first," "second," or the like, which are used in the description and the claims of the present disclosure, are not intended to indicate or imply the relative importance or implicitly indicate the amount of the features. Thus, the features defined by "first," "second," may explicitly indicate or implicitly includes at least one feature. In the description of the present disclosure, Unless otherwise defined, "a plurality of" means two or more.

The inventors have found that the current biomolecule detection, e.g., gene sequencing and protein detection, is mainly based on fluorescence labeling detection. The fluorescent labeling detection method has the problem that the cost of the detection reagent is too high, which is not conducive to the popularization and promotion in the fields of medicine, etc. The inventors have conducted in-depth research and a large number of experiments and found that the above gene sequencing is performed by different fluorophore modifications on various bases. When these bases are paired with gene fragments to be tested, fluorophores are released, and the base type can be determined by adoption of an optical system to detect the fluorescent color, and finally the sequence of the gene fragment to be tested can be obtained. The above protein detection is to label protein molecules by adoption of the technology such as fluorescent labeling or isotope labeling, and finally determine the protein type and structure by detecting the signal of the label group. As the above detection method requires different fluorescent labels, dye labels, isotope labels or the like for various bases or molecules to be tested, the cost of the detection reagent is greatly increased, which is disadvantageous for the popularization and promotion of various biomolecule detection experiments in medicine and other fields. Therefore, while ensuring the detection accuracy, the biomolecule detection is realized without complicated fluorescent labeling and the like on the biomolecules (not requiring special labeling), so the reagent cost is greatly reduced and the pre-detection processing flow is simplified, thereby facilitating the popularization and promotion in the fields such as medicine.

The embodiments of the present disclosure are described in detail below, and the examples of the embodiments are illustrated in the drawings, wherein the same or similar reference numerals are used to refer to the same or similar elements or elements having the same or similar functions. The embodiments described below with reference to the accompanying drawings are illustrative, are only intended to illustrate the present disclosure, and shall not be construed as the limitation of the present disclosure.

In one aspect of the present disclosure, the present disclosure provides a biosensor, which comprises: a sensing substrate, in which a plurality of sensing cantilevers arranged in an array are disposed on the sensing substrate and a recognition marker is disposed on the sensing cantilever; and a detection substrate, in which the detection substrate includes a plurality of optical detection components arranged in an array, the optical detection components are in one-to-one correspondence with the sensing cantilevers, the optical detection component includes a photodiode and a TFT and the photodiode is connected with the TFT.

As shown in FIG. 1, the biosensor comprises: a housing 100, a sensing substrate 300 and a detection substrate 400. According to the embodiment of the present disclosure, the housing 100 defines a sensing space 200, and at least one part of the housing 100 is configured to allow visible light (as shown by arrows in the figure) to be incident into the housing 100. According to the embodiment of the present disclosure, the sensing substrate 300 is disposed in the housing 100; a plurality of sensing cantilevers 310 arranged in an array are disposed on the sensing substrate 300; a recognition marker 311 is disposed on the sensing cantilever 310; and the sensing cantilever 310 is configured to be irradiated by the visible light incident into the housing 100. According to the embodiment of the present disclosure, the detection substrate 400 is arranged in the housing 100 and disposed on a side of the sensing substrate 300 away from an incident direction of the visible light; the detection substrate 400 includes a plurality of optical detection components 500 arranged in an array; and the optical detection components 500 are in one-to-one correspondence with the sensing cantilevers 310. According to the embodiment of the present disclosure, the optical detection component 500 includes a photodiode 600 and a TFT 700; and the photodiode 600 is connected with the TFT 700. The biosensor can detect biomolecules to be tested without complicated fluorescent labeling on the biomolecules, and hence can greatly reduce the reagent cost and improve the detection accuracy.

Simple description will be given below to a sensing principle of the biosensor provided by the embodiment of the present disclosure to facilitate understanding:

After a sample enters the housing 100, if the sample contains a determinand, a specific reaction occurs between the determinand and the recognition marker 311 on the sensing cantilever 310 and the determinand is combined with the recognition marker 311 on the sensing cantilever 310, so the sensing cantilever 310 is bent due to the combination of the determinand. Thus, before and after the combination of the determinand and the sensing cantilever 310, the intensity of visible light received at the optical detection component 500 changes, then affecting the photocurrent of the photodiode 600. The photodiode 600 is connected with the TFT 700, thereby affecting a current signal outputted by the TFT 700. Therefore, the detection of the determinand can be realized by the photoelectric conversion process. Due to the photoelectric conversion process, the intensity of light irradiated to the photodiode 600 can be changed by only combining specifically the determinand with the recognition marker 311, so the fluorescent labeling and recognition process is not involved. Therefore, whether there is determinand in the sample can be directly monitored independent of a fluorescent marker. The inventors have unexpectedly discovered that the sensing substrate 300 and the detection substrate 400 may be obtained by simple and convenient improvement of the structure of an array substrate in a thin-film transistor liquid crystal display (TFT-LCD). The accuracy of the current TFT-LCD manufacturing process is enough to satisfy the demand of the biosensor provided by the embodiment of the present disclosure, so the biosensor may be manufactured based on the conventional TFT-LCD production line, and then the production equipment cost of the biosensor can be greatly reduced.

Figure 2:
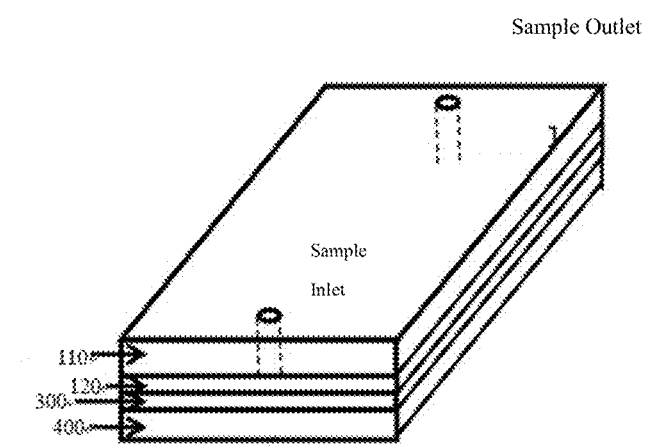
FIG. 2 is a schematic structural outside view of the biosensor provided by an embodiment of the present disclosure.

According to the embodiment of the present disclosure, the specific shape and material of the housing 100 are not specifically limited, as long as an enclosed space (a sensing space 200) for accommodating the sample may be defined, and the sample may make contact with the sensing cantilever in the sensing space 200. For instance, the housing 100 may be a rectangular housing, and the sensing substrate 300 and the detection substrate 400 are disposed in the housing; or as shown in FIG. 2 (a structural outside view of the biosensor), the housing 100 may be a transparent cover for defining the sensing space 200 at a side of the sensing substrate 300 away from the detection substrate 400. For instance, the housing 100 further includes a cover plate 110 and a flow channel wall 120, and a sample inlet and a sample outlet are disposed on the cover plate 110 and configured to supply the sample to the sensing space 200 and realize the flow of the sample in the sensing space, thereby improving the sensing efficiency and effect. The flow channel wall 120 is the side wall of the biosensor and defines a flow channel through which the sample (e.g., liquid) flows in the sensing space 200.

According to the embodiment of the present disclosure, a top of the cover plate 110 or the housing 100 may be made from transparent materials, and the visible light may be incident into the housing 100 through the cover plate 110. It should be noted that the specific material of the cover plate 110 is not specifically limited, as long as the transparent condition and the condition of not reacting with the sample are satisfied. For instance, according to the embodiment of the present disclosure, the material may be at least one of glass or polymer. According to the embodiment of the present disclosure, the flow channel wall 120 is a retaining wall surrounding the biosensor and is configured to define the sensing space 200. It should be noted that the specific material of the flow channel wall 120 is not specifically limited, may be selected by those skilled in the art according to actual demands, and for instance, may be at least one of silicon oxide, silicon nitride or polymer. According to the embodiment of the present disclosure, both the sample inlet and the sample outlet are through holes processed on the cover plate 110 and are respectively used for sample addition and outflow. According to the embodiment of the present disclosure, the specific type of the determinand in the sample is not specifically limited and, for instance, may be at least one of biomolecules such as enzyme and antigen.

Figure 3:
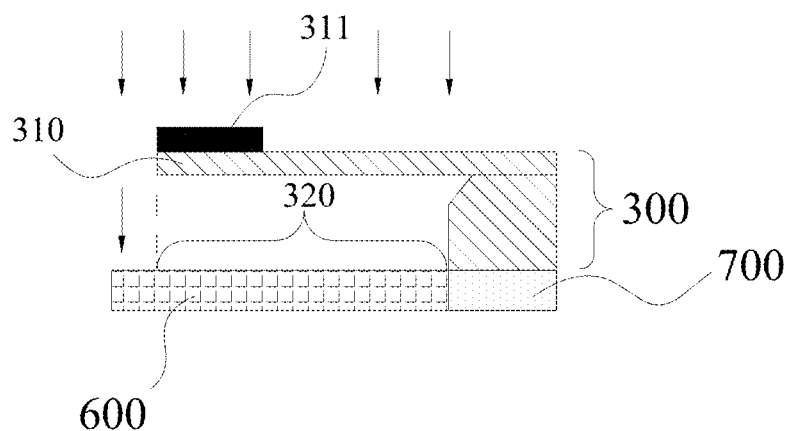
FIG. 3 is a schematic structural view of a biosensor provided by an embodiment of the present disclosure.

According to the embodiment of the present disclosure, as shown in FIG. 3, a projection of the sensing cantilever on the detection substrate (a sensing cantilever projection 320) coincides with at least one part of the photodiode 600 along the incident direction of the visible light (as shown by arrows in the figure). It should be understood by those skilled in the art that a part of the sensing cantilever projection 320 coinciding with the photodiode 600 is not irradiated by the visible light as the visible light is shielded by the sensing cantilever 310; and a region except a coincided part of the sensing cantilever projection 320 and the photodiode 600 may be irradiated by the visible light as the visible light may run through. According to the embodiment of the present disclosure, the recognition marker 311 is disposed on the sensing cantilever 310 and reacts specifically with the determinand in the sample. According to the embodiment of the present disclosure, the specific type of the specific reaction is not specifically limited and, for instance, may be at least one of enzyme and substrate reaction or antigen and antibody reaction.

Figure 4:
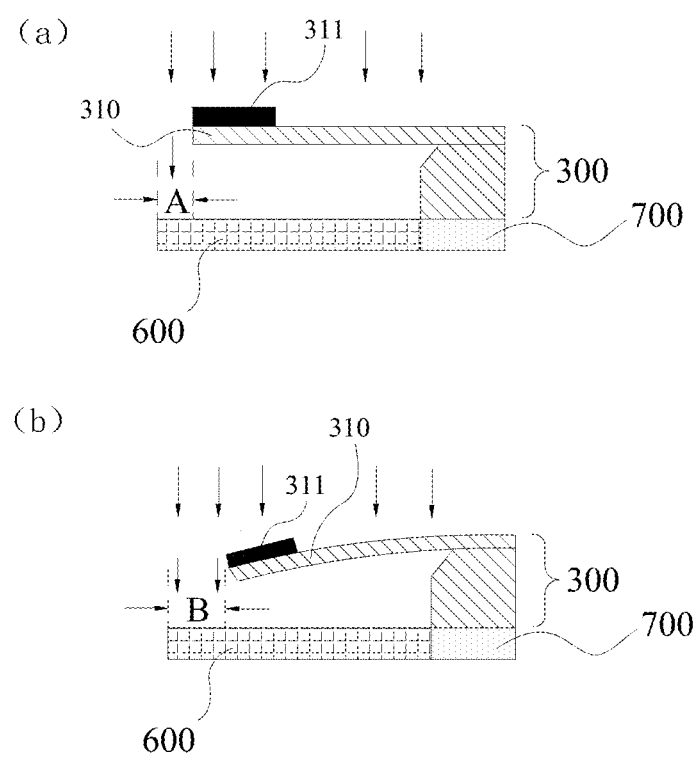
FIG. 4 is a schematic diagram illustrating a part of flows of utilizing the biosensor for biosensing in an embodiment of the present disclosure.

According to the embodiment of the present disclosure, as shown in FIG. 4, the sensing cantilever 310 is configured to bent towards the detection substrate 400 (not shown in the figure) after the determinand reacts with the recognition marker 311. Thus, the detection performance of the biosensor can be realized by utilization of the photoelectric sensing technology with high accuracy. Schematically, the optical detection component 500 comprises photodiodes 600 arranged in an array and controlled by TFTs 700. The photodiode 600 may sense the intensity of the visible light irradiated thereon and convert the intensity into an electrical signal. The sensing cantilever 310 acts as a light-shielding plate of the photodiode 600. In the case of detection, the degree of curvature of the sensing cantilever 310 changes, so the shielding area for the photodiode 600 changes, and then the electrical signal read by the photodiode 600 change. Schematically, as shown in (a) in FIG. 4, before the determinand reacts with the recognition marker 311, the sensing cantilever 310 is in the unbent state, and the visible light irradiates parts except the sensing cantilever projection 320 (not shown in the figure), that is, an area of a portion of the photodiode 600 irradiated by the visible light is A; at this point, a light receiving area of the photodiode 600 is A; and the photodiode 600 may record the light intensity at this point. As shown in (b) in FIG. 4, after the determinand reacts with the recognition marker 311, the degree of curvature of the sensing cantilever 310 changes; the sensing cantilever is bent towards a direction of the photodiode 600; the area of the photodiode 600 irradiated by the visible light is converted into B; at this point, the light receiving area of the photodiode 600 is B; and the photodiode 600 may record the light intensity at this point. It should be understood by those skilled in the art that as the sensing cantilever 310 is bent, the area of the photodiode 600 irradiated by the visible light is increased, namely, the light receiving area of the photodiode 600 is B which is greater than A; the light intensity of the visible light irradiated thereon sensed by the photodiode 600 is also correspondingly increased; the photodiode 600 converts the change of the light intensity into a readable electrical signal; and the detection result can be obtained after analysis.

Figure 5:
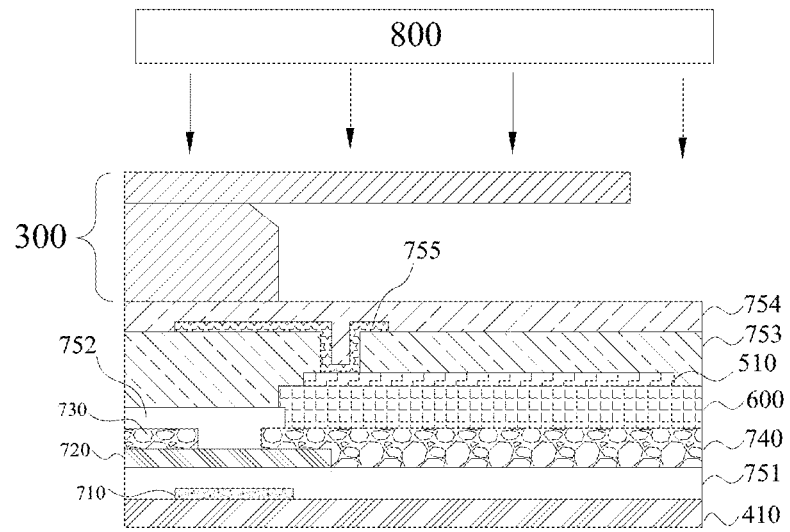
FIG. 5 is a schematic structural view of a biosensor provided by an embodiment of the present disclosure.

According to the embodiment of the present disclosure, as shown in FIG. 5, the detection substrate 400 further includes a base 410; the plurality of optical detection components 500 are arranged in an array on the base 410; and the optical detection component 500 further includes: a gate electrode 710, an active layer 720, a source electrode 730, a drain electrode 740, a photodiode 600 and a common electrode 510. According to the embodiment of the present disclosure, the gate electrode 710 is disposed on the base 410; the active layer 720 is disposed on a side of the gate electrode 710 away from the base 410; the source electrode 730 and the drain electrode 740 are insulated from each other and disposed on a side of the active layer 720 away from the gate electrode 710; the photodiode 600 is disposed on a side of the drain electrode 740 away from the active layer 720 and connected with the drain electrode 740; and the common electrode 510 is disposed on a side of the photodiode 600 away from the drain electrode 730 and connected with the photodiode 600. The specific position of the parts in the optical detection component 500 is consistent with the structure of an array substrate, so the optical detection component can be manufactured by utilization of the manufacturing process of the array substrate, and then the production cost can be reduced.

According to the embodiment of the present disclosure, the photodiode 600 may be made from an amorphous silicon material. The amorphous silicon material is sensitive to light, so the sensitivity of the biosensor provided by the embodiment of the present disclosure can be guaranteed. The amorphous silicon material is also a common material for manufacturing a TFT on the array substrate, so the production of the photodiode in the embodiment of the present disclosure by utilization of the amorphous silicon material is favorable for production by utilization of equipment for manufacturing the array substrate, and then the equipment cost can be further saved.

According to the embodiment of the present disclosure, the biosensor further comprises at least one of the following structures: a first insulating layer 751, a second insulating layer 752, a third insulating layer 753, a pixel electrode 755 and a planarization layer 754. According to the embodiment of the present disclosure, the first insulating layer 751 is disposed on a side of the gate electrode 710 away from the base and completely covers the gate electrode 710, so that the gate electrode 710 can be insulated from other structures. The second insulating layer 752 is disposed on a side of the source electrode 730 and the drain electrode 740 away from the active layer and configured to insulate the source electrode 730 from the drain electrode 740. The third insulating layer 753 is disposed on a side of the second insulating layer 752 and the common electrode 510 away from the base 410 and has the function of insulating. According to the embodiment of the present disclosure, a through hole is formed in the third insulating layer 753; the pixel electrode 755 is disposed on a side of the third insulating layer 753 away from the common electrode 510; and the pixel electrode 755 is connected with the common electrode 510 via the above-mentioned through hole. Thus, the performance of the biosensor can be further improved. According to the embodiment of the present disclosure, the planarization layer 754 is disposed on a side of the pixel electrode 755 away from the third insulating layer 753 and has the function of planarization and insulating. That is to say, the sensing substrate of the biosensor provided by the embodiment of the present disclosure can be obtained by arranging the photodiode and the sensing cantilever on an array substrate of a display device. Therefore, the biosensor can be obtained by additionally arranging the photodiode and the sensing substrate on the basis of manufacturing the array substrate; or the array substrate may be directly purchased and then the photodiode and the sensing substrate are additionally arranged on the array substrate. Therefore, the biosensor provided by the embodiment of the present disclosure may comprise a pixel electrode 755, a passivation layer (not shown in the figure) and other structures of the array substrate.

According to the embodiment of the present disclosure, in order to further improve the sensing effect of the biosensor, the biosensor may further comprises a light source 800. The light source 800 is configured to irradiate visible light to the inside of the housing 100. As the biosensor provided by the embodiment of the present disclosure is sensitive to the visible light, in the case of sufficient external light, natural light may be used to realize sensing. In order to increase a photocurrent of the photodiode when not being sensed, the light intensity of the visible light incident into the housing 100 can also be improved through an independently arranged light source 800. Therefore, the performance of the biosensor can be further improved.

According to the embodiment of the present disclosure, the photodiode 600 is connected with the drain electrode 740 of the TFT 700. The detection substrate 400 further comprises: a plurality of gate lines 520, a plurality of source lines 530 and a common electrode 510. According to the embodiment of the present disclosure, the gate line 520 is connected with the gate electrodes 710 of the plurality of TFTs 700 disposed in the same row or the same column; the source line 530 is connected with the source electrodes 730 of the plurality of TFTs 700 disposed in the same row or the same column; and the common electrode 510 is connected with a terminal of the photodiode 600 not connected with the TFT 700. Therefore, the performance of the biosensor can be further improved.

Figure 6:
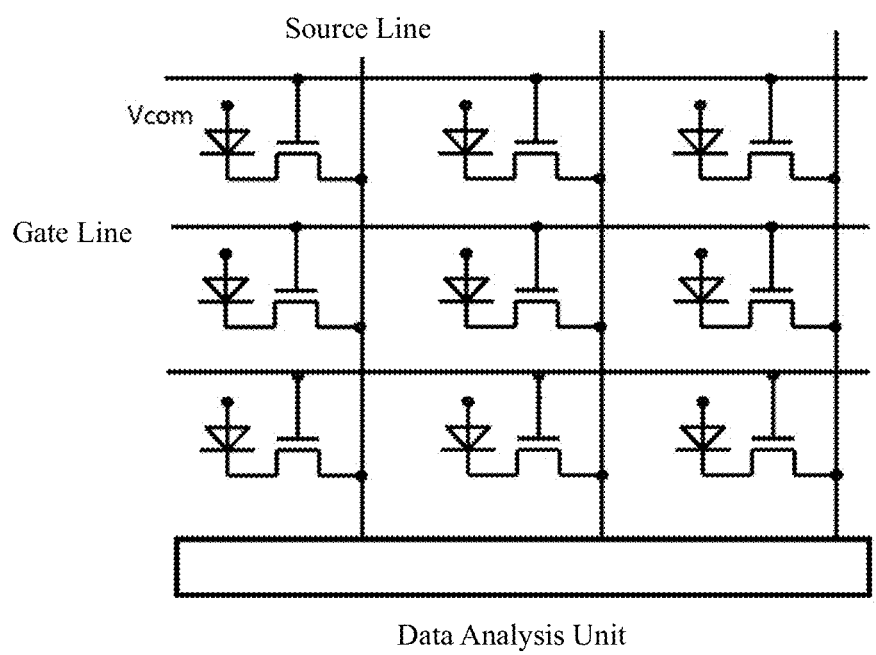
FIG. 6 is a schematic structural view of a detection substrate in a biosensor provided by an embodiment of the present disclosure.

According to the embodiment of the present disclosure, as shown in FIG. 6, the biosensor further comprises a data analysis unit 900, and the data analysis unit 900 is connected with the plurality of source lines 740. According to the embodiment of the present disclosure, the optical detection components 500 in the detection substrate 400 are arranged in an array, and each optical detection component 500 is the photodiode 600 controlled by the TFT 700. According to the embodiment of the present disclosure, the specific type of the photodiode 600 is not specifically limited; and for instance, the photodiode may be a PIN junction photodiode. According to the embodiment of the present disclosure, a lower end of the photodiode 600 is connected with the source electrode 730 of the TFT 700, and the source lines 530 are connected with the source electrodes 730 of the plurality of TFTs 700 disposed in the same row or the same column. An upper end of the photodiode 600 is connected with the same common voltage (Vcom). The photodiode 600 can convert the intensity change of the visible light irradiated thereon into the change of the quantity of electric charge. The change of the quantity of electric charge is transmitted to the TFT 700 connected with the photodiode 600 and then affects a source current of the TFT 700. The change of the source current is transmitted to the data analysis unit 900 through the source line, and then the change of the electrical signal can be read and whether there is determinand in the sample can be determined.

Figure 7:
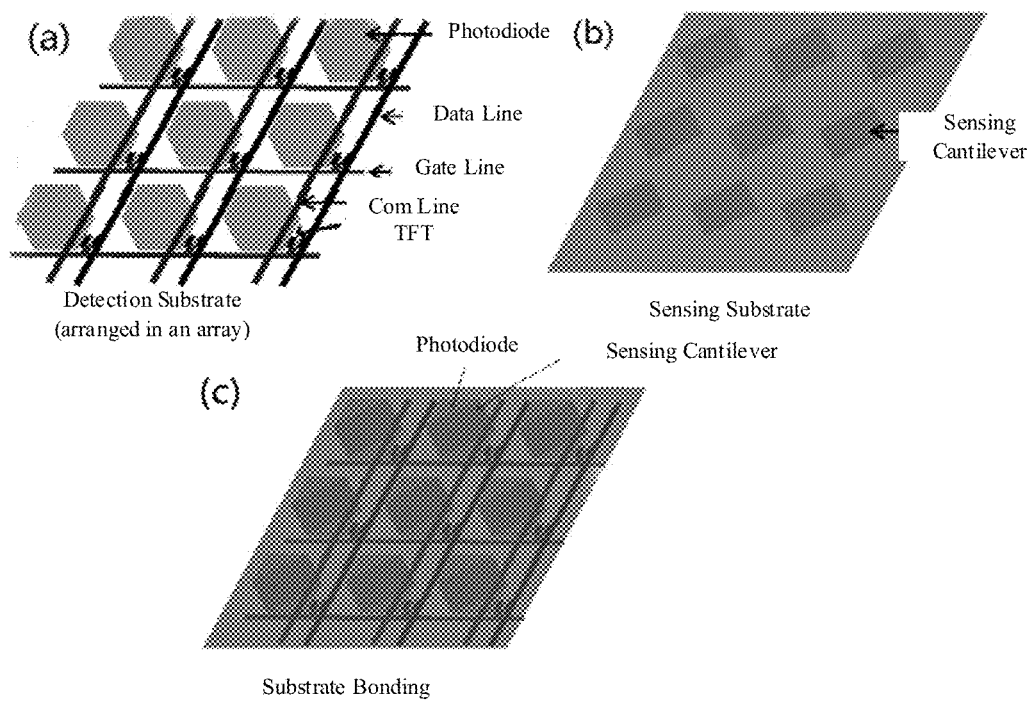
FIG. 7 is a schematic structural view of an optical detection array circuit in a biosensor provided by an embodiment of the present disclosure.

According to the embodiment of the present disclosure, as shown in FIG. 7, in the detection substrate 400, the specific shape of the photodiode 600 in the optical detection component 500 is not specifically limited, may be designed by those skilled in the art as required, and for instance, as shown in (a) in FIG. 7, may be a regular hexagon in the figure. According to the embodiment of the present disclosure, the optical detection components 500 are not required to be tightly arranged, and a certain gap is left to facilitate the flow of the sample in the sensing space 200, as long as there is certain directly opposite area between the detection cantilever and the photodiode. According to the embodiment of the present disclosure, the specific size of the optical detection component 500 is not specifically limited. For instance, the size may range from tens to hundreds of microns. According to the embodiment of the present disclosure, as shown in (a)-(c) in FIG. 7, the photodiode may be additionally arranged on the array substrate to form the detection substrate as shown in (a) in FIG. 7; the sensing substrate as shown in (b) in FIG. 7 is manufactured by utilization of the MEMS technology capable of realizing the precision processing of Si-based material; and the detection substrate 400 and the sensing substrate 300 are bonded to finally obtain the structure as shown in (c) in FIG. 7. In the obtained bonding structure, a projection of the sensing cantilever 310 on the detection substrate 400 coincides with at least one portion of the photodiode 600. Therefore, the performance of the biosensor can be further improved.

In summary, the biosensor can detect the biomolecules to be tested without complicated fluorescent labeling on the biomolecules, and hence can greatly reduce the reagent cost and improve the detection accuracy.

In another aspect of the present disclosure, the present disclosure provides a method for manufacturing a biosensor. According to the embodiment of the present disclosure, the biosensor manufactured by the method may be the foregoing biosensor. According to the embodiment of the present disclosure, the method comprises:

Providing a sensing substrate.

In the step, the sensing substrate is arranged in a housing; a plurality of sensing cantilevers arranged in an array are disposed on the sensing substrate; a recognition marker is disposed on the sensing cantilever, and the sensing cantilever is configured to be capable of being irradiated by visible light incident into the housing. According to the embodiment of the present disclosure, the sensing substrate arranged in the step may be the foregoing sensing substrate and then has the same structures, materials, characteristics and advantages with the foregoing sensing substrate. According to the embodiment of the present disclosure, the plurality of sensing cantilevers arranged in an array can be obtained by utilization of MEMS technology capable of realizing the precision processing of Si-based materials; and subsequently, the sensing substrate in the embodiment of the present disclosure can be obtained by arranging a specific recognition marker on each sensing cantilever.

Providing a detection substrate.

In the step, the detection substrate is arranged in the housing and disposed on a side of the sensing substrate away from the incident direction of the visible light; the detection substrate includes a plurality of optical detection components arranged in an array; the optical detection components are in one-to-one correspondence with the sensing cantilevers; the optical detection component includes a photodiode and a TFT which are connected with each other; and the detection substrate is manufactured based on an array substrate of a display panel. Thus, the biosensor can be conveniently obtained. The biosensor manufactured by the method may have the same characteristics and advantages with the foregoing biosensor. In summary, the biosensor manufactured by the method may be manufactured based on the manufacturing process of the array substrate, and the manufactured biosensor can detect the biomolecules without complicated fluorescent labeling on the biomolecules, and hence can greatly reduce the reagent cost and improve the detection accuracy. According to the embodiment of the present disclosure, the detection substrate arranged in the step may be the foregoing detection substrate and then has the same structure, materials, characteristics and advantages with the foregoing detection substrate.

The method for manufacturing the biosensor further comprises:

S100: providing a housing.

In the step, the housing defines a sensing space, and at least one portion of the housing is configured to allow the visible light to be incident into the housing. According to the embodiment of the present disclosure, the housing provided in the step may be the foregoing housing of the biosensor and then has the same structure, materials, characteristics and advantages with the foregoing housing.

Figure 8:
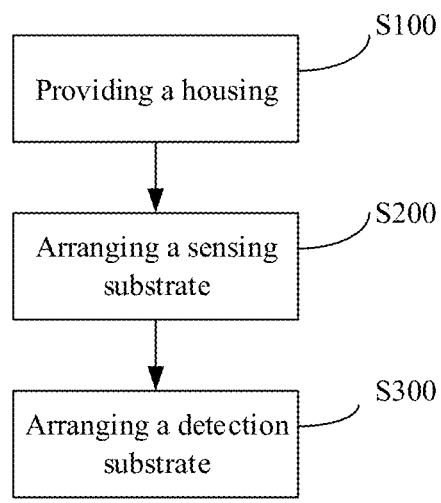
FIG. 8 is a flowchart of a method for manufacturing a biosensor, provided by an embodiment of the present disclosure.

The illustrative manufacturing method, as shown in FIG. 8, comprises providing a housing and arranging a sensing substrate and a detection substrate.

In the embodiment of the present disclosure, the housing may be provided before providing the sensing substrate and the detection substrate, and then the sensing substrate and the detection substrate are arranged in the housing; or the sensing substrate and the detection substrate may be provided at first, and then the housing is provided and the two substrates are placed in the housing.

According to the embodiment of the present disclosure, the method for manufacturing the biosensor further comprises at least one of the following steps:

S1: arranging a light source.

In the step, the light source is configured to irradiate visible light to the inside of the housing. Therefore, the performance of the biosensor manufactured by the method can be further improved.

S2: arranging a data analysis unit.

In the step, a TFT in the detection substrate is connected to the data analysis unit through a signal line such as a source line. Therefore, the performance of the biosensor manufactured by the method can be further improved.

In summary, the biosensor manufactured by the method can be the foregoing biosensor and then has all the characteristics and advantages of the foregoing biosensor. The biosensor manufactured by the method can detect the biomolecules to be tested without complicated fluorescent labeling on the biomolecules, and hence can greatly reduce the reagent cost and improve the detection accuracy.

Figure 9:
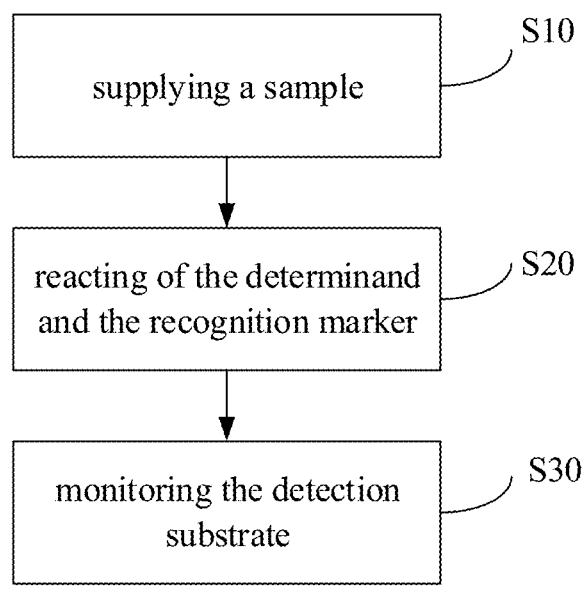
FIG. 9 is a flowchart of a biosensing method by utilizing a biosensor provided by an embodiment of the present disclosure.

In still another aspect of the present disclosure, the present disclosure provides a biosensing method by utilizing the foregoing biosensor. As shown in FIG. 9, the method comprises:

S10: supplying a sample.

In the step, a sample is supplied to the housing, which is conducive to the reaction of the determinand and the recognition marker in the next step.

S20: reacting of the determinand and the recognition marker.

In the step, the determinand in the sample reacts with the recognition marker on the sensing cantilever, so that the sensing cantilever is bent. According to the embodiment of the present disclosure, in the step, the specific working principle of the sensing cantilever has be described above in detail, so no further description will be given here.

S30: monitoring the detection substrate.

In the step, the electrical signal of the detection substrate before and after the bending of the sensing cantilever are monitored; whether there is determinand in the sample is determined; and then biosensing can be realized. Therefore, the foregoing biosensor may be conveniently utilized for biosensing, can detect the biomolecules to be tested without complicated fluorescent labeling on the biomolecules, and hence can greatly reduce the reagent cost and improve the detection accuracy. According to the embodiment of the present disclosure, whether there is determinand in the sample is determined by comparing the change of the source current of the TFT in the optical detection component on the detection substrate before and after supplying the sample to the housing. Therefore, the performance of utilizing the foregoing biosensor for biosensing can be further improved. According to the embodiment of the present disclosure, the specific process of the step of monitoring the detection substrate has been described above in detail, so no further description will be given here.

In summary, the biosensing method by utilizing the forgoing biosensor has at least one of the following advantages: the precision of the photoelectric sensor technology in the optical detection component is high; the detection accuracy is high; the reagent cost is greatly reduced; or complicated fluorescent labeling is not required.

The present application claims priority of Chinese Patent Application No. 201710415425.2 filed on Jun. 5, 2017, the disclosure of which is incorporated herein by reference in its entirety as part of the present application.

The invention claimed is:

1. A biosensor, comprising:
 a sensing substrate, a plurality of sensing cantilevers arranged in an array being disposed on the sensing substrate, and a recognition marker being disposed on each of the plurality of sensing cantilevers; and
 a detection substrate, including a plurality of optical detection components arranged in an array,
 wherein the plurality of optical detection components are in one-to-one correspondence with the plurality of sensing cantilevers, each of the plurality of optical detection components includes a photodiode and a thin-film transistor, and the photodiode is connected with the thin-film transistor,
 wherein each of the plurality of sensing cantilevers is configured to be irradiated by visible light; and
 a projection of each of the plurality of sensing cantilevers on the detection substrate coincides with at least one portion of the photodiode along an incident direction of the visible light,
 wherein the recognition marker has a capability of performing a specific reaction with a determinand in a sample, and each of the plurality of sensing cantilevers is configured to be bent towards the detection substrate after the determinand reacts with the recognition marker,
 wherein under a condition that each of the plurality of sensing cantilevers is in the unbent state, an area of a portion of the photodiode corresponding to the sensing cantilever irradiated by the visible light is A, and under each of the plurality of sensing cantilevers is bent towards a direction of the photodiode corresponding to the sensing cantilever because of the specific reaction between the determinand and the recognition marker, an area of the photodiode irradiated by the visible light is B, B is larger than A.

2. The biosensor according to claim 1, further comprising:
 a housing, defining a sensing space, at least one portion of the housing being configured to allow the visible light to be incident into the housing,
 wherein the sensing substrate and the detection substrate are arranged in the housing, and the detection substrate is disposed on a side of the sensing substrate away from the incident direction of the visible light.

3. The biosensor according to claim 2, wherein the photodiode is made from amorphous silicon.

4. The biosensor according to claim 2, wherein the photodiode is connected with a drain electrode of the thin-film transistor; and
the detection substrate further includes:
a plurality of gate lines, connected with gate electrodes of a plurality of thin-film transistors disposed in a same row or a same column;
a plurality of source lines, connected with source electrodes of a plurality of thin-film transistors disposed in a same row or a same column; and
a common electrode, connected with a pole of the photodiode not connected with the thin-film transistor.

5. The biosensor according to claim 4, further comprising at least one of the following:
a light source, configured to irradiate the visible light to an inside of the housing; and
a data analysis unit, connected with the plurality of source lines.

6. The biosensor according to claim 2, wherein the detection substrate further includes a base, the plurality of optical detection components are arranged in an array on the base; and each of the plurality of optical detection components includes:
a gate electrode, disposed on the base;
an active layer, disposed on a side of the gate electrode away from the base;
a source electrode and a drain electrode, insulated from each other and disposed on a side of the active layer away from the gate electrode;
a photodiode, disposed on a side of the drain electrode away from the active layer and connected with the drain electrode; and
a common electrode, disposed on a side of the photodiode away from the drain electrode and connected with the photodiode.

7. A method for manufacturing a biosensor, comprising:
providing a sensing substrate, wherein a plurality of sensing cantilevers arranged in an array are disposed on the sensing substrate and a recognition marker is disposed on each of the plurality of sensing cantilevers; and
providing a detection substrate, wherein the detection substrate includes a plurality of optical detection components arranged in an array, the plurality of optical detection components are in one-to-one correspondence with the plurality of sensing cantilevers, each of the plurality of optical detection components includes a photodiode and a thin-film transistor, and the photodiode is connected with the thin-film transistor; and
wherein the detection substrate is manufactured based on an array substrate of a display panel,
wherein each of the plurality of sensing cantilevers is configured to be irradiated by visible light; and
a projection of each of the plurality of sensing cantilevers on the detection substrate coincides with at least one portion of the photodiode along an incident direction of the visible light,
wherein the recognition marker has a capability of performing a specific reaction with a determinand in a sample, and each of the plurality of sensing cantilevers is configured to be bent towards the detection substrate after the determinand reacts with the recognition marker,
wherein under a condition that each of the plurality of sensing cantilevers is in the unbent state, an area of a portion of the photodiode corresponding to the sensing cantilever irradiated by the visible light is A, and under each of the plurality of sensing cantilevers is bent towards a direction of the photodiode corresponding to the sensing cantilever because of the specific reaction between the determinand and the recognition marker, an area of the photodiode irradiated by the visible light is B, B is larger than A.

8. The method for manufacturing the biosensor according to claim 7, further comprising:
providing a housing; and
arranging the sensing substrate and the detection substrate in the housing, in which the detection substrate is disposed on a side of the sensing substrate away from an incident direction of the visible light.

9. The method according to claim 8, further comprising at least one of a following steps:
arranging a light source, in which the light source is configured to irradiate visible light to an inside of the housing; and
arranging a data analysis unit, in which the data analysis unit is connected with a thin-film transistor in the detection substrate.

10. A biosensing method by utilizing the biosensor according to claim 1, comprising:
supplying a sample to the housing;
allowing each of the plurality of sensing cantilevers to be bent under a condition that a determinand in the sample reacts with the recognition marker on each of the plurality of sensing cantilevers; and
monitoring an electrical signal of the detection substrate before and after bending of each of the plurality of sensing cantilevers, determining whether there is determinand in the sample, so as to realize biosensing.

11. The biosensing method according to claim 10, wherein the determining whether there is determinand in the sample is performed by comparing change of a source current of the thin-film transistor in the optical detection component on the detection substrate before and after supplying the sample to the housing.

12. The biosensor according to claim 3, further comprising:
a housing, defining a sensing space, at least one portion of the housing being configured to allow the visible light to be incident into the housing,
wherein the sensing substrate and the detection substrate are arranged in the housing, and the detection substrate is disposed on a side of the sensing substrate away from the incident direction of the visible light.

13. The method for manufacturing the biosensor according to claim 7, further comprising:
providing a housing; and
arranging the sensing substrate and the detection substrate in the housing, in which the detection substrate is disposed on a side of the sensing substrate away from an incident direction of the visible light.

14. The biosensing method according to claim 11, wherein each of the plurality of sensing cantilevers is configured to be irradiated by visible light; and
a projection of each of the plurality of sensing cantilevers on the detection substrate coincides with at least one portion of the photodiode along an incident direction of the visible light.

15. The biosensing method according to claim 11, wherein the recognition marker has a capability of performing a specific reaction with a determinand in a sample, and each of the plurality of sensing cantilevers is configured to be bent towards the detection substrate after the determinand reacts with the recognition marker.

16. The biosensing method according to claim 11, further comprising:
a housing, defining a sensing space, at least one portion of the housing being configured to allow the visible light to be incident into the housing,
wherein the sensing substrate and the detection substrate are arranged in the housing, and the detection substrate is disposed on a side of the sensing substrate away from the incident direction of the visible light.

* * * * *